United States Patent [19]
Mayer

[11] Patent Number: 5,513,515
[45] Date of Patent: May 7, 1996

[54] METHOD FOR MEASURING PERMEABILITY OF A MATERIAL

[75] Inventor: William N. Mayer, White Bear Lake, Minn.

[73] Assignee: Modern Controls, Inc., Minneapolis, Minn.

[21] Appl. No.: 440,703

[22] Filed: May 15, 1995

[51] Int. Cl.$^6$ .................................................. G01N 15/08
[52] U.S. Cl. ................................................................ 73/38
[58] Field of Search ............................ 73/38, 37, 19.01, 73/866

[56] References Cited

U.S. PATENT DOCUMENTS

| | | | |
|---|---|---|---|
| 3,590,634 | 7/1971 | Pasternack et al. | 73/38 |
| 3,604,246 | 9/1971 | Toren | 73/38 |
| 3,618,361 | 11/1971 | Stephens et al. | 73/38 |
| 4,464,927 | 8/1984 | Reid | 73/38 |
| 4,656,865 | 4/1987 | Callan | 73/38 |

OTHER PUBLICATIONS

Article: "Measuring Gas Permeability of Plastic Films," Walter Soroka, *Canadian Packaging*, Aug. 1979, pp. 17 & 19.

Article: "Permeation Speeds Tests, Aids Choice of Exact Material," Murray, Dorschner, *Package Engineering*, Mar. 1983, pp. 76–80.

Article: "Permeability of Plastics," Carl W. Hall, Technical/Engineering Methods, Research, Testing, Nov. 1973, pp. 53–57.

Article: "Factors Affecting the Oxygen Barrier of Vinylidene Chloride–Vinyl Chloride Copolymers," Phillip T. Delassus, Saran and Converted Products Research, The Dow Chemical Company, Midland, Michigan 48640, "Plastics in Packaging," Nov. 1978, pp. 78–82.

*Primary Examiner*—Michael J. Brock
*Attorney, Agent, or Firm*—Palmatier, Sjoquist & Helget

[57] ABSTRACT

A method for measuring the permeability of a gas through a material, wherein the steps include exposing the material to the gas to be measured and measuring the outgassing characteristics of the material over increments of time, to develop exponential expressions representative of the measured amounts, and solving the exponential expressions for the diffusion coefficient D and the solubility coefficient S; and then calculating the permeability of the material by forming the product of the diffusion coefficient D and the solubility coefficient S.

5 Claims, 2 Drawing Sheets

METHOD FOR MEASURING PERMEABILITY OF A MATERIAL

BACKGROUND OF THE INVENTION

The present invention relates to a method and apparatus for measuring the permeability of certain barrier materials to any gas. More particularly, a preferred embodiment of the invention relates specifically to a method for measuring the oxygen permeability of a flat sample barrier film material.

Certain apparatus for measuring the oxygen flow rate through a membrane barrier material are known in the prior art. For example, U.S. Pat. No. 3,618,361, issued Nov. 9, 1971, discloses an early system for measuring the gas permeability of a film. Similarly, U.S. Pat. No. 3,590,634, issued Jul. 6, 1971, discloses another instrument for measuring permeation rates through a membrane. U.S. Pat. No. 4,467,927, issued Aug. 14, 1984, discloses an apparatus for measuring gas transmission through films in multiple test cells. All of these devices operate in conjunction with an oxygen detector which typically provides an electrochemical transformation in response to the presence of oxygen. One such oxygen detector is disclosed in U.S. Pat. No. 3,223,597, issued Dec. 14, 1965, and another form of oxygen detector is disclosed in U.S. Pat. No. 4,085,024, issued Apr. 18, 1978. All of these earlier patents, and a considerable number of more recent patents, utilize a test cell setup in conjunction with an oxygen detector to derive an electrical signal which is representative of the amount of oxygen with in a given chamber of the test cell. A sample of the barrier material undergoing test is typically clamped within the test cell to form two chambers, wherein one chamber is initially free of oxygen and filled with a neutral gas such as nitrogen, and the other chamber is initially saturated with oxygen. Before proceeding with these initial conditions, it is first necessary to outgas all oxygen from the material sample undergoing tests. Outgasing is accomplished by flowing a neutral gas such as nitrogen through both chambers described above, monitoring the test gas for oxygen content until it appears that the oxygen content has become depleted to zero, or near zero, and then proceeding with the initial conditions described above. The test process requires that the neutral test gas flow be monitored until the oxygen concentration in the test gas reaches a steady state level, which can require many hours of operation. In general, the amount of time required for such a test is directly related to the permeability coefficient of the material and to the material thickness. The permeability coefficient is directly related to temperature and, to a lesser extent, pressure. The objective of tests of this type is to measure the amount of oxygen which permeates through the test membrane under steady state conditions, and the oxygen measurements are typically made by devices such as are disclosed in the foregoing prior art patents.

The large majority of permeation measurements now being made are in terms of the amount of gas permeating a given sample. This may be a container or an essentially flat sample. The answers are given in terms of the volume or weight of a gas permeating the sample in a given time. In the case of a container, this becomes the volume or weight of gas per time per container. In the case of a flat sample, it is the volume or weight of a gas per time per unit area. These answers are obtained and referred to the conditions of the test. In a formal way, these are not permeation values but are transmission rate values for that gas, through that sample under the specific test conditions.

For example:

$$7.5 \frac{cc}{M^2 \cdot day}$$

The definition of the permeation rate for a film (in the same units) is referred to a standard temperature and pressure (STP) (760 mm Hg, 0° C.) for a 1 mil film. The amount of gas being transferred is roughly inversely proportional to the film thickness. At the test conditions, a 1 mil film would then transmit ten times as much $O_2$ as a 10 mil sample.

$$\text{Transmission Rate (1 mil)} = 75 \frac{cc}{M^2 \cdot day}$$

Correction to 0° C. would then result in the formally defined permeation rate.

Basically, the permeation of gas through a material results from the inherent physical characteristics of the material. These characteristics have been formally defined in all of the literature in the field for the last 30 years. These characteristics are: the solubility of the gas of interest in the material and the rate of diffusion of the gas through the material. The solubility is the volume of gas which will dissolve in a like volume of the material $$\left( i.e. \frac{cc}{cm^3} \right)$$

and the diffusion coefficient denotes the rate at which the gas moves through the material $$\left( i.e. \frac{cm^2}{sec} \right).$$

The product of the solubility coefficient and the diffusion coefficient is called the permeability coefficient; and in this case, the units are $$\left( \frac{cc}{cm^3} \frac{cm^2}{sec} \right)$$

thus:

$$P \left( \begin{array}{c} \text{permeability} \\ \text{coefficient} \end{array} \right) \frac{cc}{cm^3} \frac{cm^2}{sec} = S \left( \begin{array}{c} \text{solubility} \\ \text{coefficient} \end{array} \right) \frac{cc}{cm^3} D \left( \begin{array}{c} \text{Diffusion} \\ \text{coefficient} \end{array} \right) \frac{cm^2}{sec}$$

The relationship between P and $\bar{P}$ ms simply a unit conversion factor which is $$\text{Conversion factor} = 2.94 \times 10^{-12}$$

so that:

$$P = \frac{\bar{P}}{2.94 \times 10^{-12}} \frac{cc}{M^2 \cdot day}$$

As noted above, this information is well known. All aspects have been reviewed for years in the literature on the subject of permeation. The background is necessary, however, to follow the new method of measurement of the transmission of gas through a material.

The most used present method of measurement today is termed isostatic. This refers to the case in which a sample is mounted in such a way that one side of the sample is exposed to the gas of interest. The other side is isolated at zero, or extremely low levels, of that gas. In this way, the gas permeating the sample can be measured as a function of time.

Usually the film is first outgased by flowing a neutral gas over both sides of the sample. Then the permeant gas is made to flow on one side. The final answer is obtained by waiting until the permeant gas level on the sensor side reaches a steady state value. These times become quite long for even moderately good barriers. For instance, a PET film, 10 mil ($10^{-2}$ inches) thick, at 30° C., has a transmission value of approximately 7.5 cc/$M^2$·day. Many barriers today are at least one-tenth of this value. Even so, the outgasing for the 10 mil sample will take about 21 hours; and the permeation measurement requires about 29 hours.

It would be extremely desirable if the amount of time required for making valid permeation measurements could be significantly reduced. The equipment required for making such measurements is fairly expensive and complex; and therefore, the measurement of a single sample of material can require the exclusive use of such equipment for a period of several days. If a significant number of samples require measurement, the number of test stations set up with the necessary equipment for such measurements must be multiplied to fit the testing schedule. Therefore, any modification through the overall process which can be made by way of shortening the total test time will be of great advantage and significance in the field.

SUMMARY OF THE INVENTION

The present invention comprises a method for measuring the transmission rate and permeability of varying materials in a radically shortened period of time. The method is carried out by the same equipment as was formerly used for such measurements, but the results are achieved by measuring the outgasing characteristics of the material rather than subjecting the material to the two stages of outgasing and then measuring permeability. The method is derived from the recognition that the permeability characteristics of the material can be predictably determined by analysis of the complex, non-linear, behavior of the material during the outgasing process and the recognition that permeability of the material is directly related to the material's outgasing characteristics. Briefly, the method steps comprise outgasing a gas-saturated material and observing the exponential rate of decay of the outgased gas over a predetermined interval of time. It has been found empirically that the outgasing curve of a material is the sum of two exponentials, and points along these exponential curves for a given material can be measured to yield a measurement of the materials diffusion constant "D" and solubility constant "S." Once these constants are measured, the transmission rate through the material is readily derived mathematically.

Application of the present method to known materials will result in an overall decrease in the required measurement time interval by a factor of about 40 and will result in a sensitivity improvement of about a factor of 4, when compared with the existing methods in the prior art. Of course, these comparison numbers will vary somewhat with the type of material selected.

Accordingly, it is a principal object and advantage of the present invention to provide a measure of the transmission rate and permeability of a material in a much shorter time interval than is known in the prior art.

It is another object and advantage of the present invention to provide such a measurement with a much higher degree of sensitivity than is possible in the prior art.

Other and further objects and advantages of the invention will become apparent from the following specification and claims and with reference to the appended drawings.

DESCRIPTION OF THE PREFERRED EMBODIMENT

Figure 1:
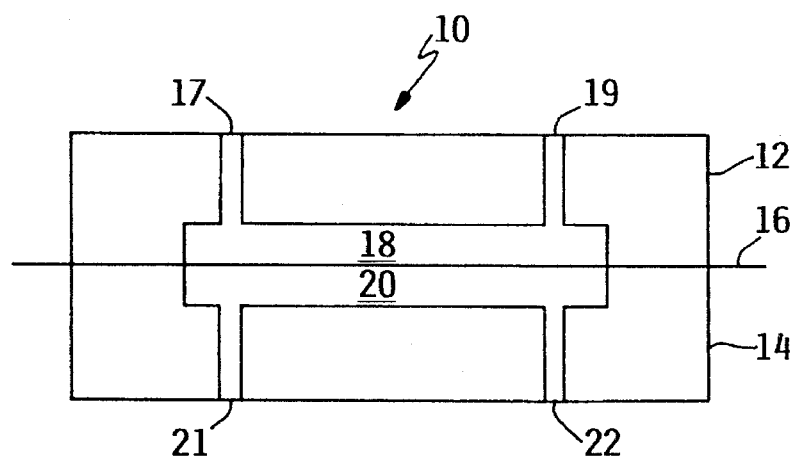
FIG. 1 shows a diagrammatic representation of an isostatic measurement cell.

Referring first to FIG. 1 of the drawings, there is shown a diagrammatic representation of an isometric measurement cell 10 of the type typically used for prior art gas transmission and permeability measurements. Cell 10 is typically formed of an upper cell housing 12 and a lower cell housing 14 which may be tightly clamped together, with the plastic membrane sample 16 clamped between the two housings 12 and 14. After the membrane sample 16 is clamped between the housings 12 and 14, there is formed a chamber 18 adjacent the upper surface of the membrane 16 and a chamber 20 adjacent the lower surface of the membrane 16. Chamber 18 has a gas inlet 17 and a gas outlet 19, and chamber 20 has a gas inlet 21 and a gas outlet 22. In operation, a neutral gas such as nitrogen is passed through chamber 20 via inlet 21 and outlet 22, and is conveyed to a suitable gas detector via a conduit connected to outlet 22. The permeant gas is passed through chamber 18 via inlet 17 and outlet 19, and the amount of such permeant gas that passes through membrane 16 can be measured by the gas detector connected to outlet 22.

A preliminary outgassing step must be performed before the foregoing measurement process can take place, to ensure that no permeant gas is contained in chamber 20 or is saturated into the membrane 16. This preliminary outgassing step is accomplished by first connecting both sides of the measurement cell 10 to a neutral gas supply, and flowing the neutral gas through both chambers 18 and 20. The outgassing step is also measured by the gas detector, which will detect a gradually reduced quantity of permeant gas as the neutral gas flows through both sides of the measurement cell 10. When the gas detector detects a sufficiently low quantity of permeant gas as a result of this step, the neutral gas flow through chamber 18 can be replaced by permeant gas flow through chamber 18, and the measurement or permeation step of the process can begin.

Figure 2:
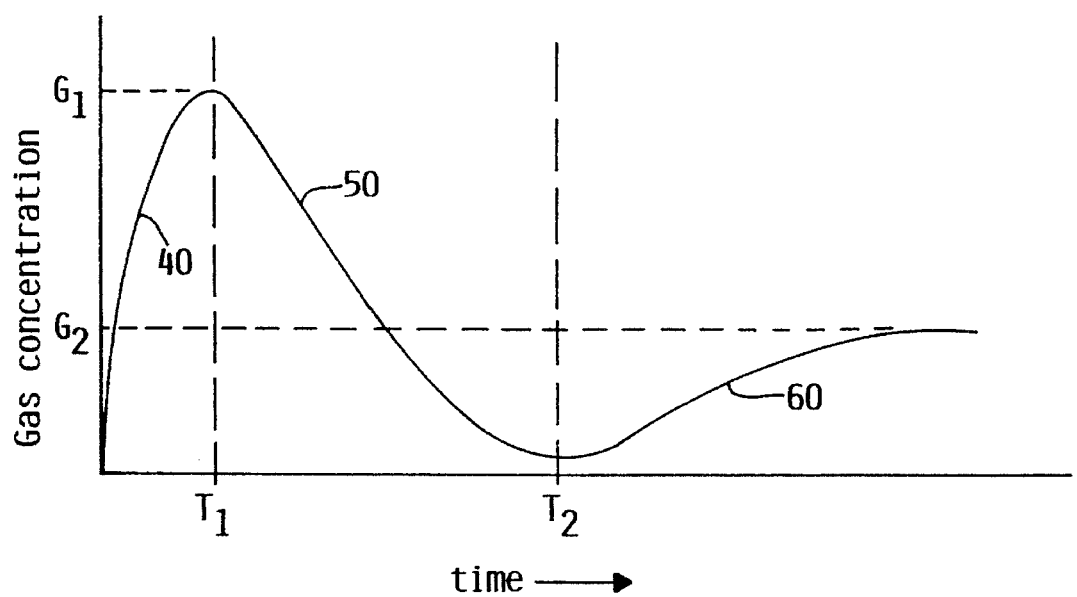
FIG. 2 shows the time-related curve for measuring gas concentration.

FIG. 2 shows a time curve to illustrate both the outgassing step and the permeation step for a typical measurement process. The outgassing step continues until time T2, which is determined by monitoring the gas concentration level measured by the gas detector, and waiting until the measured concentration level has decreased to a very low, nearly zero, measurement. This is shown by curve 50 in FIG. 2, which is an exponentially decaying curve. At time T2 the neutral gas flow through chamber 18 is replaced with permeant gas flow through chamber 18, and the gas detector continues to monitor permeant gas concentration levels in chamber 20. The permeant gas in chamber 20 will slowly rise to a steady-state level G2, which is representative of the steady-state gas transmissivity of the permeant gas through membrane 16. This is shown by curve 60 in FIG. 2, which is an exponentially rising curve. As a result of this measurement, the permeability of membrane 16 can be calculated.

In the prior art, for high barrier films (i.e., low permeation), it typically requires about 20 hours for the outgassing step to be performed and about another 30 hours for the permeability measurement step to be performed.

Referring again to FIG. 2, it has been observed that the initial part of the outgassing step produces a sharply-rising gas measurement, illustrated by curve 40, followed by a more gradually-reducing gas measurement curve 50 throughout the outgassing step. The sharply-rising measurement occurs until about time $T_1$, and is attributed in part to the measurement delay of the gas detector. The gas detector provides a measurement which peaks at a gas concentration level G1, and then begins an exponential drop until time $T_2$, when the outgassing step is discontinued. The observation and analysis of this phenomena has led to the development of the present invention which will be described hereinafter.

Initially, it is recognized that the outgassing of a membrane is controlled by the diffusion rate through the membrane, and if outgassing is observed only on one side of the membrane it must be realized that the outgassing measurement is made for only one-half the thickness of the membrane material; i.e., it must be assumed that the other side of the membrane is outgassing at the same rate. It can be empirically determined that outgassing follows an exponential curve, or the sum of a number of exponential curves, which relate to the diffusion constant "D" and the solubility coefficient "S" of the material. By using curve fitting techniques it is possible to solve for the exponential curves and to calculate a value for the permeability of the material. It has been found empirically that the outgassing curve 50 of FIG. 2 is a sum of two exponential curves of the form $Ke^{-xt}$.

Figure 3:
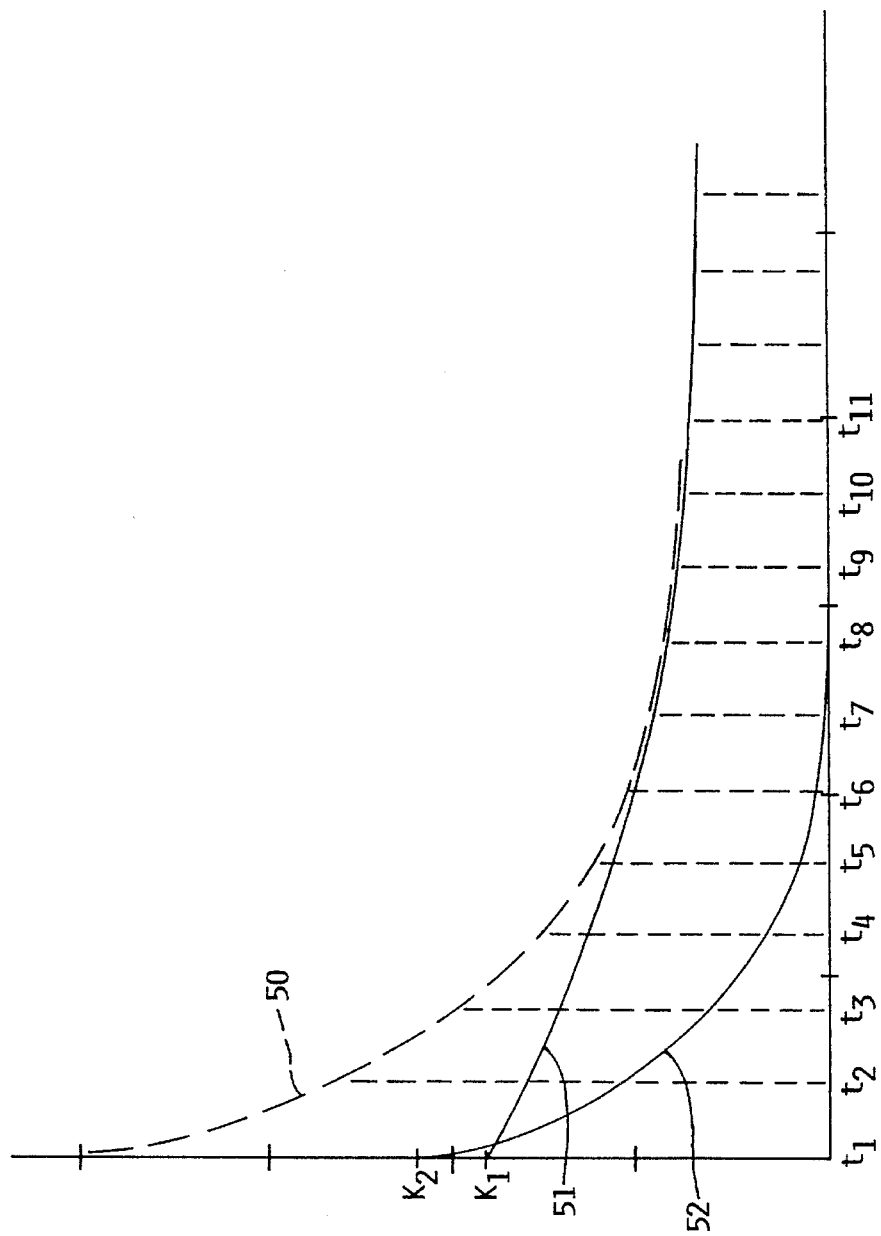
FIG. 3 shows an expanded view of a portion of the curve of FIG. 2.

FIG. 3 shows an expanded portion of the curve of FIG. 2, illustrating a portion of the outgassing curve 50 on an expanded time scale. In particular, this portion of the outgassing curve can be empirically shown to be the sum of the exponential curves 51 and 52, where curve 51 is in the form $$y_1(t) = K_1 e^{-at}$$

and curve 52 is in the form $$Y_2(t) = K_2 e^{-bt}$$

so that curve 50 can be represented by the equation $$y(t) = y_1(t) + y_2(t) = K_1 e^{-at} + K_2 e^{-bt}.$$

The value of the exponents "a" and "b" can be determined empirically, by a curve fitting process applied to actual measurement results. After time $t_7$ (see FIG. 3) the second term in the foregoing equation becomes small enough to be ignored, and the function reduces essentially to $y(t) = K_1 e^{-at}$. The exponent "a" is related to the diffusion coefficient D for the particular material, according to the equation $$a = 2.4 \, D/l^2$$

where 1 is ½ the thickness of the particular material. Therefore, the exponential equation after time $t_7$ simplifies to $$y(t) = K_1 e(-2.4D/l^2) \text{ or } K_1 \exp(-2.4D/l^2)t$$

If we define a value $A = e^{-at}$, where $A \leq 1$, then $Ln\, A = -at$, and the foregoing equation becomes $$Ln\, A = 2.4Dt/l^2$$

Solving for the diffusion coefficient D:

$$D = (Ln\, A) \, l^2/2.4\, t$$

the time value t is the time increment required for measuring A, or referring to FIG. 3, the time increment $(t_8-t_7)$, $(t_9-t_8)$, $(t_{10}-t_9)$, etc.

In a practical application of the method, the foregoing assumptions can be made only after a sufficient time has passed so that one of the exponential curves has reduced to essentially zero. This time can be measured or determined by utilizing the known relationship of the rate of decay of an exponential curve over time, i.e., the ratio of the logarithmic values of two successive points along an exponential curve, taken at uniform time increments, is a constant value. Therefore, the observed curve 50 can be measured at successive equal time increments $t_2, t_3, \ldots t_6, t_7, t_8$, and the respective logarithmic values can be calculated and compared. When two successive logarithmic values become equal, it then becomes apparent that the curve 50 is behaving like a pure single exponential curve, and not the sum of two or more exponential curves. As indicated above, this procedure would show curve 50 to be a single exponential curve after about time $t_7$, and the foregoing calculations could be made to determine the constant $K_1$ and the diffusion coefficient D.

The constant $K_1$ is the value of $y_1(t)$ at time $t=0$, which can be determined by working backward from the measured value at time $t_7$; i.e., the time at which curve 50 begins behaving like a single exponential curve, as described above. For an exponential curve it is known that the rate of decay of the curve over equal increments of time is $$\frac{y(t_n)}{Y(t_{n-1})}$$

for every increment of time $[t_n - t_{n-1}]$. It is also known that at time $t=0$ the equation $K_1 e^{-at} = K_1$. Therefore, in the foregoing example, where $t_n = t_7$, there are 7 equal increments of time between the value $y_7(t)$ and $y_1(t) = K_1$. Therefore, $K_1$ is equal to $$K_1 = \frac{y(t_7)}{[y(t_7)/y(t_6)]^7}$$

This equation can be solved for $K_1$ since all of the "y" values are measured values.

After the foregoing steps yield the solution to the equation $$y_1(t) = K_1 \, e^{-at}$$

the remaining term of the overall equation can be determined by a subtractive process, wherein the calculated $y_1(t)$ curve is subtracted from the measured y(t) curve 50 of FIG. 3, to find the values $Y_2(t)$ for the various time points $t_2, t_3, t_4, \ldots t_{10}$. These values enable a determination of the exponent $-bt$ in the equation $$y_2(t) = K_2 \, e^{-bt}.$$

If we set the value B such that $B = e^{-bt}$, then $Ln\, B = -bt$, where $B \leq 1$, and $(Ln\, B)/t = -b$, which can be solved for the various time points shown on FIG. 3. The value $K_2$ can also be determined at the time $t=0$, and therefore the second exponential term $y_2(t)$ becomes known.

Once the two exponential terms have been determined the solubility coefficient S can be determined by integrating the y(t) curve to provide a measure of the gas volume under the y(t) curve, and comparing this gas volume with the total volume of the material or film from which this gas volume emanated, using the equation $$S = \frac{\int K_1 e^{-at} + K_2 e^{-bt}}{V_f}$$

where $V_f$=volume of the film, which can be measured. The value $S$ so determined is then multiplied by the value $D$ previously determined, to yield the permeability $\overline{P}$, by the equation $$\overline{P} = S \cdot D.$$

The permeability $P$ of the film can then be determined by applying the previously described constant to the foregoing result, or $$P = \overline{P}/2.94 \times 10^{-12}.$$

In operation, the foregoing method is practiced by first exposing the test film to the gas to be measured, i.e., oxygen to cause the gas to be absorbed into the film. Next, the film is placed into a test chamber of the type shown in FIG..1, and a neutral gas such as nitrogen is flowed through one of the chambers 18 or 20, and the other chamber is closed to any flow. The neutral gas, carrying the outgassing oxygen component, is conveyed to an oxygen detector of the types known in the prior art, and the outgassing curve 50 is measured as a function of time. At equal times $t_2, t_3, t_4 \ldots$ the ratio of the logarithmic values of the curve is compared until the ratio of two successive values becomes equal to one. The $y_1(t)$ curve is then determined according to the methods disclosed herein, and then the $y_2(t)$ curve is determined. The diffusion coefficient $D$ is thus determined, and the integration process described herein yields the solubility coefficient $S$. These values, combined as described herein, yield the permeability $P$ for the particular film sample which is being tested. Of course, as is well known in this art, the process described herein is influenced by temperature, pressure and relative humidity variations. It may be necessary to correct the final results derived according to the present process to account for such changes, or to normalize the result to a "standard" temperature and pressure, if such is the practice in the particular industry where the method is used.

The present invention may be embodied in other specific forms without departing from the spirit or essential attributes thereof; and it is, therefore, desired that the present embodiment be considered in all respects as illustrative and not restrictive, reference being made to the appended claims rather than to the foregoing description to indicate the scope of the invention.

What is claimed is:

1. A method for measuring the permeability of a gas through a material, comprising the steps of:
   a) exposing the material to the gas to be measured;
   b) measuring the amount of said gas which is outgassed from said material over successive equal increments of time; and forming a curve plot which represents the outgassed amount vs. time;
   c) developing an exponential expression which matches said curve plot, said exponential expression comprising the sum of two exponent terms in the form of $K_1 e^{-at} + K_2 e^{-bt}$;
   d) utilizing one of said exponent terms to calculate the diffusion coefficient $D$ of said material;
   e) calculating the solubility coefficient $S$ of said material by integrating said exponential expression over all time and dividing by the volume of said material; and
   f) calculating the permeability $P$ of said material by forming the product of the diffusion coefficient $D$ and the solubility coefficient $S$.

2. The method of claim 1, further comprising, after step (b), the step of comparing the logarithmic values of the measured amount at successive equal time increments until such comparison equals unity at two successive time increments, and then performing step c) utilizing measured amounts from successive time increments.

3. The method of claim 2, further comprising, after step c), the step of calculating the second exponent term by subtracting the first exponent term from the measured amount at successive time intervals.

4. The method of claim 2, wherein the step of utilizing one of said exponent terms to calculate the diffusion coefficient $D$ further comprises the step of relating the diffusion coefficient $D$ to the exponent value "a" by the equation $$a = 2.4 \, D/l^2$$

where $l$ is one-half the thickness of said material, to form the exponent term $$K_1 \exp -(2.4 D/l^2)t.$$

5. A method for measuring the permeability of a test gas through a material, comprising the steps of:
   a) absorbing the test gas into the material;
   b) placing the material into a chamber filled with neutral gas and measuring the amount of test gas which is outgassed from the material over successive equal increments of time;
   c) forming the logarithmic value of each of the measured amounts for each of the successive increments of time and comparing successively formed logarithmic values to identify a time $T$ when two successive logarithmic values are substantially equal;
   d) developing an exponential expression of the form $K_1 e^{-at}$ which matches the test gas measured amounts after time $T$;
   e) calculate the diffusion coefficient $D$ from the expression $K_1 e^{-at}$ using the equation $$D = \frac{a \, l^2}{2.4} \quad \text{where } l \text{ is}$$

where $l$ is ½ the thickness of said material;
   f) developing an exponential expression of the form $K_2 e^{-bt}$ by subtracting the expression $K_1 e^{-at}$ from the measured amounts for all times $t$ less than $T$, to form the expression $K_1 e^{-at} + K_2 e^{-bt}$ which is representative of said measured amounts for all times $t$;
   g) integrating said exponential expression $k_1 e^{-at} + K_2 e^{-bt}$ over all times $t$, and dividing said integrated result by the volume of said material, to find the solubility coefficient $S$; and
   h) forming the product $S*D$ to find the permeability of said material.

\* \* \* \* \*

UNITED STATES PATENT AND TRADEMARK OFFICE
CERTIFICATE OF CORRECTION

PATENT NO. : 5,513,515
DATED : May 7, 1996
INVENTOR(S) : William N. Mayer

It is certified that error appears in the above-indentified patent and that said Letters Patent is hereby corrected as shown below:

Column 2, line 1, insert after "For example:" the following --

Sample - 10 mil flat film (PET)

Transmission Rate for $O_2$:

$7.5 \dfrac{cc}{M^2 \cdot day}$ at one atmosphere

Pressure, 30°C and less than 5% RH. --

Column 2, line 3, delete "$7.5 \dfrac{cc}{M^2 \cdot day}$"

Column 2, line 47, "ms" should be -- is --.

Signed and Sealed this

Twenty-ninth Day of October 1996

BRUCE LEHMAN

*Attest:*

*Attesting Officer*   Commissioner of Patents and Trademarks